(12) United States Patent
Farrell et al.

(10) Patent No.: US 12,233,218 B2
(45) Date of Patent: Feb. 25, 2025

(54) URINARY CATHETER DRAINAGE MEMBERS AND CATHETERS HAVING THE SAME AND METHODS OF FORMING CATHETERS

(71) Applicant: Hollister Incorporated, Libertyville, IL (US)

(72) Inventors: David J. Farrell, Ballina (IE); Brent H. Sellers, Libertyville, IL (US); David A. Knauz, Riverwoods, IL (US); Padraig M. O'Flynn, Ballina (IE); Paul M O'Donnell, Castlebar (IE); John Hayes, Drogheda (IE); Gilberto Marchetti, Mundelein, IL (US); Horacio Montes de Oca Balderas, Ballina (IE)

(73) Assignee: Hollister Incorporated, Libertyville, IL (US)

(*) Notice: Subject to any disclaimer, the term of this patent is extended or adjusted under 35 U.S.C. 154(b) by 467 days.

(21) Appl. No.: 17/617,836

(22) PCT Filed: Jul. 31, 2020

(86) PCT No.: PCT/US2020/044477
§ 371 (c)(1),
(2) Date: Dec. 9, 2021

(87) PCT Pub. No.: WO2021/025992
PCT Pub. Date: Feb. 11, 2021

(65) Prior Publication Data
US 2022/0233812 A1    Jul. 28, 2022

Related U.S. Application Data

(60) Provisional application No. 62/883,719, filed on Aug. 7, 2019.

(51) Int. Cl.
*A61M 25/00* (2006.01)
*B29C 65/54* (2006.01)

(52) U.S. Cl.
CPC ...... *A61M 25/0017* (2013.01); *A61M 25/001* (2013.01); *A61M 25/0069* (2013.01); *B29C 65/54* (2013.01); *A61M 2202/0496* (2013.01)

(58) Field of Classification Search
CPC ............ A61M 25/0017; A61M 25/001; A61M 25/0069; A61M 2202/0496; A61M 27/00;
(Continued)

(56) References Cited

U.S. PATENT DOCUMENTS 3,602,228 A    8/1971    Cowley
3,720,210 A    3/1973    Diettrich
(Continued)

FOREIGN PATENT DOCUMENTS

CN    108066883 A    5/2018
DE    2729566 A1    1/1979
(Continued)

OTHER PUBLICATIONS

Bubleach, Connector with Tube, Oct. 9, 1991, machine translation (Year: 1991).*
(Continued)

*Primary Examiner* — Philip R Wiest
*Assistant Examiner* — Brandon W. Levy
(74) *Attorney, Agent, or Firm* — Cook Alex Ltd.

(57) ABSTRACT

A catheter drainage member (112) configured to be attached to a catheter tube (116), the drainage member comprising: body (115) having an inner surface (114); a well (120) defined by the inner surface of the body, the well configured to receive the catheter tube and an adhesive (122); and wherein the well is configured to selectively distribute the adhesive between the inner surface and the tube.

8 Claims, 5 Drawing Sheets

(58) Field of Classification Search
CPC .......... A61M 25/0014; A61M 25/0068; A61M 25/0097; A61M 25/008; A61M 2025/0073; A61M 25/0009; A61M 25/0032; A61M 25/0043; A61M 2025/1093; A61M 39/12; A61M 25/00; A61M 2025/0098; B29C 65/54; B29C 65/1406; B29C 65/524; B29C 66/21; B29C 66/71; B29C 66/1222; B29C 66/1224; B29C 66/5344; B29C 65/4845; B29C 65/52; B29C 66/1226; B29C 66/322; B29C 65/4835; B29C 66/50; B29C 66/51; B29C 66/53; B29C 66/534; B29K 2995/0056; B29K 2023/06; B29L 2031/7542

See application file for complete search history.

(56) References Cited

U.S. PATENT DOCUMENTS

| | | | |
|---|---|---|---|
| 3,903,887 | A | 9/1975 | Antoshkiw |
| 4,068,659 | A | 1/1978 | Moorehead |
| 4,068,660 | A | 1/1978 | Beck |
| 4,194,509 | A | 3/1980 | Pickering et al. |
| 4,222,384 | A | 9/1980 | Birtwell |
| 4,657,536 | A | 4/1987 | Dorman |
| 4,695,276 | A | 9/1987 | Shinno et al. |
| 4,701,162 | A | 10/1987 | Rosenberg |
| 4,781,703 | A | 11/1988 | Walker et al. |
| 4,802,947 | A | 2/1989 | Bartholomew |
| 4,883,470 | A | 11/1989 | Haindl |
| 5,017,259 | A | 5/1991 | Kohsai |
| 5,263,945 | A * | 11/1993 | Byrnes .................. A61M 39/12 604/905 |
| 5,269,755 | A | 12/1993 | Bodicky |
| 5,360,418 | A | 11/1994 | Weilbacher et al. |
| 5,772,636 | A | 6/1998 | Brimhall et al. |
| 5,876,376 | A * | 3/1999 | Schwab ............ A61M 25/1034 604/103 |
| 5,954,702 | A * | 9/1999 | Lal .................... B29C 66/52297 604/905 |
| 6,482,180 | B2 | 11/2002 | Toyokawa et al. |
| 6,496,737 | B2 | 12/2002 | Rudie et al. |
| 6,575,959 | B1 | 6/2003 | Sarge et al. |
| 6,632,204 | B2 | 10/2003 | Guldfeldt et al. |
| 7,789,873 | B2 | 9/2010 | Kubalak et al. |
| 8,241,245 | B2 | 8/2012 | Markel et al. |
| 9,878,125 | B2 | 1/2018 | Dye |
| 9,993,636 | B2 | 6/2018 | Uber, III et al. |
| 2001/0005782 | A1 | 6/2001 | Tanghoj et al. |
| 2002/0026163 | A1 | 2/2002 | Grundke |
| 2003/0135197 | A1 * | 7/2003 | Wang ....................... C08J 5/121 264/102 |
| 2005/0033237 | A1 | 2/2005 | Fentress et al. |
| 2008/0027414 | A1 | 1/2008 | Tanghoj et al. |
| 2009/0187165 | A1 | 7/2009 | Kaern |
| 2012/0172848 | A1 | 7/2012 | Gustavsson et al. |
| 2014/0276393 | A1 | 9/2014 | Park et al. |
| 2015/0273183 | A1 | 10/2015 | Foley et al. |
| 2017/0000978 | A1 | 1/2017 | Murray et al. |
| 2018/0050174 | A1 * | 2/2018 | Olson .................. A61M 27/00 |
| 2018/0093085 | A1 | 4/2018 | Burkholz et al. |
| 2018/0104447 | A1 | 4/2018 | Madlung et al. |

FOREIGN PATENT DOCUMENTS

| | | | |
|---|---|---|---|
| DE | 3049612 | A1 | 7/1982 |
| EP | 0450330 | * | 10/1991 |
| GB | 1574187 | A | 9/1980 |

OTHER PUBLICATIONS

Injecting light cure adhesive: fast cure times and simple, processing improve needle joints; Retrieved from ProQuest Dialog on Oct. 16, 2018: https://dialog.proquest.com/professional/docview/1046677546accountid=157282.

International Search Report and Written Opinion Dated Nov. 17, 2020 for International Application No. PCT/US2020/044477.

* cited by examiner

URINARY CATHETER DRAINAGE MEMBERS AND CATHETERS HAVING THE SAME AND METHODS OF FORMING CATHETERS

The present application is a National Stage Entry of International Application No. PCT/US2020/044477, filed Jul. 31, 2020, which claims the benefit of and priority to U.S. Provisional Application No. 62/883,719, filed Aug. 7, 2019, all of which are hereby incorporated herein by reference.

FIELD OF THE DISCLOSURE

The present disclosure generally relates to urinary catheters. More particularly, the present disclosure relates to urinary catheter drainage members.

DESCRIPTION OF RELATED ART

Catheters are used to treat many different types of medical conditions and typically include an elongated tube that is inserted into and through a passageway or lumen of the body. Catheters, and in particular intermittent catheters, are commonly used by those who suffer from various abnormalities of the urinary system, such as urinary incontinence. Urinary catheters generally comprise a tube surface with two ends. A first end has a catheter tip; the tip may be inserted into a user's urethra. A second end generally has a funnel that is used to help facilitate drainage of bodily fluids.

Because urinary catheter drainage members are meant to be inundated with fluids, their connections to the catheter tube must be strong. Single use catheters are known to be manufactured with techniques such as insert molding and glue bonding, using UV curable glues. These glues help connect the catheter tube to the drainage member. When applying glues there are two methods known in the prior art: vertical manufacture and horizontal manufacture.

A problem with the current known manufacturing methods is that they produce imprecise and inefficient results. For example, when catheter sizes are large (i.e. Ch 18), currently known catheter drainage member designs do not have enough space for receiving the glues. Because of current drainage members' deficient designs, glue often overflows from the drainage member during manufacturing and this overflow creates a defective part. Additionally, current catheter drainage members do not have a design that allows for consistent and even application of glue when the vertical and horizontal dispensing methods are used. Uneven application may result in contamination of the catheter, rendering the catheter inoperable. Consequently, there is a need for new catheter drainage members which yield more viable connections using both the horizontal and vertical adhesive distribution methods.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, the catheter drainage member is configured to be attached to a catheter tube and includes a body having an inner surface and a well that is defined by the inner surface of the body. The well is configured to receive the catheter tube and an adhesive. The well is also configured to selectively distribute the adhesive between the inner surface and the tube.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Urinary catheter drainage members according to the present disclosure and their individual components may be variously configured without departing from the scope of the present disclosure, but in one embodiment, a urinary catheter drainage member is configured as shown in FIG. 1.

Figure 1A:
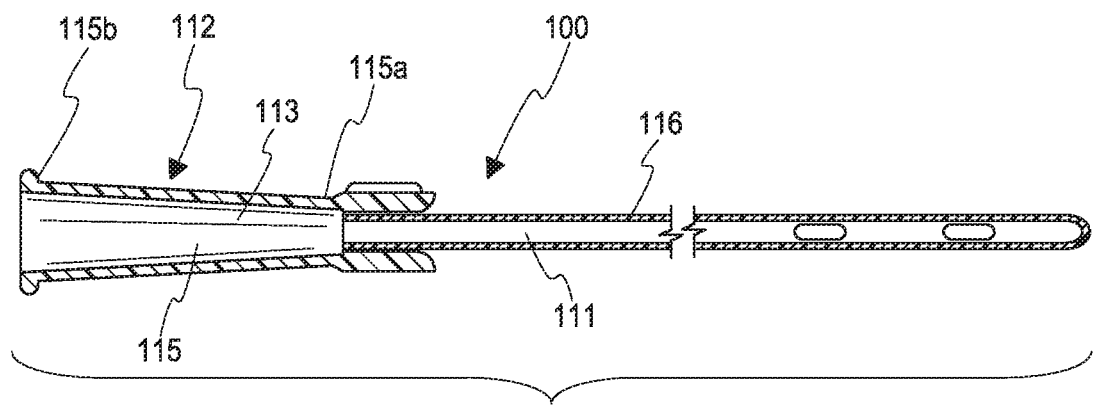
FIG. 1A is a side cross-sectional view of an embodiment of a urinary catheter showing a catheter shaft connected to a drainage member.

FIG. 1A shows an example of an embodiment of a urinary catheter 100 including a drainage member 112 connected to a catheter tube 116. The drainage member 112 includes a body 115 having a proximal 115a end and a distal end 115b. The catheter shaft 116 includes a proximal portion, a distal portion, and a drainage lumen 111. The drainage member 112 includes a lumen 113 that is fluidically connected to the catheter drainage lumen 111.

Figure 1B:
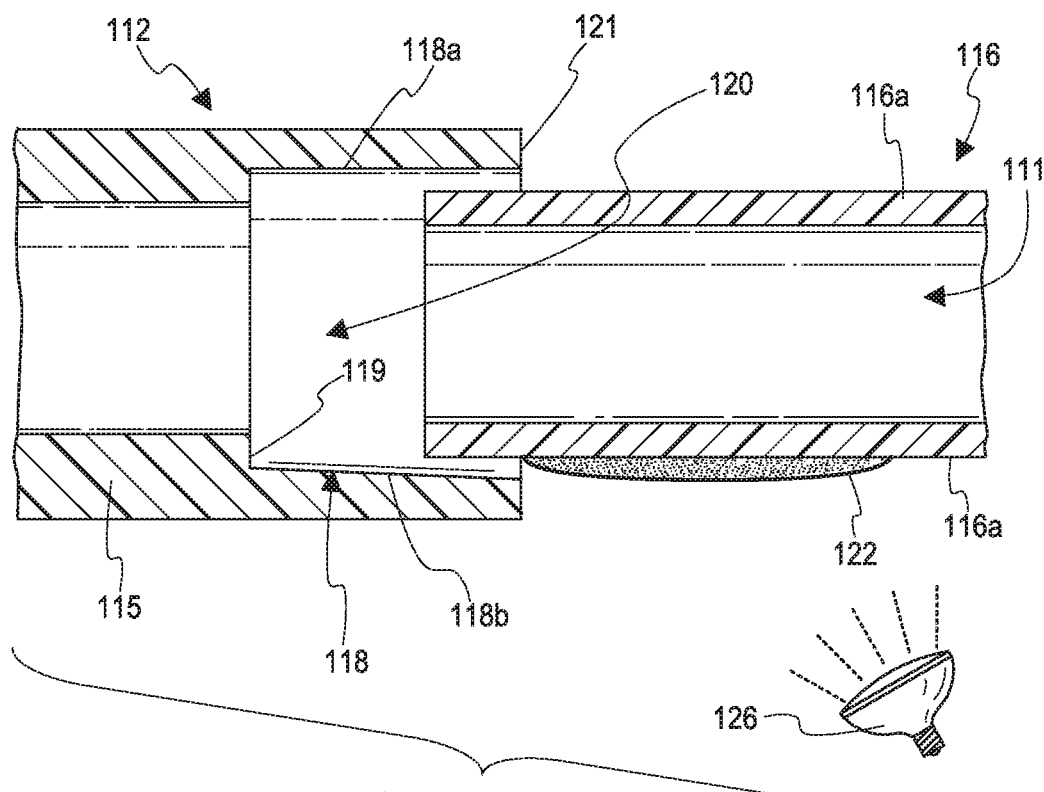
FIG. 1B is a cross-sectional view of an embodiment of a catheter drainage member having a non-symmetrical well.

FIGS. 1B and 10 show an embodiment of a urinary catheter drainage member 112 configured to be attached to a catheter tube 116. The drainage member 112 comprises a body 115 having an inner surface 114. The inner surface 114 defines a well 120 that is configured to receive the catheter tube 116 and an adhesive 122. The adhesive 122 may be any suitable adhesive for attaching the catheter tube 116 and drainage member 112 to each other. For example, the adhesive 112 may comprise a UV-light curable glue, such as Dymax adhesives 111-MSK, 1072-M, 1180-M-UR, 1406-M or Henkel adhesives Loctite 3951, 3921 or 3922. The well 120 is configured to selectively distribute the adhesive 122 between the inner surface 114 and the tube 116. The well 120 also may be configured to evenly distribute the adhesive 122. The adhesive 122 may bond the catheter tube 116 to the inner surface 114, forming a joint between the tube 116 and the drainage member 112. A gap 136 is defined between the inner surface 114 and the tube 116 (FIG. 1D). The gap 136 may be configured to receive the adhesive 122. The adhesive 122 moves or is distributed throughout the gap 136 (throughout the space between the inner surface 114 of the drainage member and the outer surface of the tube 116), as the tube 116 is inserted into the well 120. Consequently, more selectively distributed and/or evenly distributed adhesive 122 is located between the inner surface 114 and the tube 116, which assists in creating a stronger and more durable bond. This distribution of the adhesive occurs with very minimal movement between the tube 116 and the drainage member 112. For example, this distribution occurs from inserting the tube 116 into the well 120 the drainage member 112, with little or no rotation of the tube or the drainage member to distribute the adhesive within the gap 136.

Figure 1C:
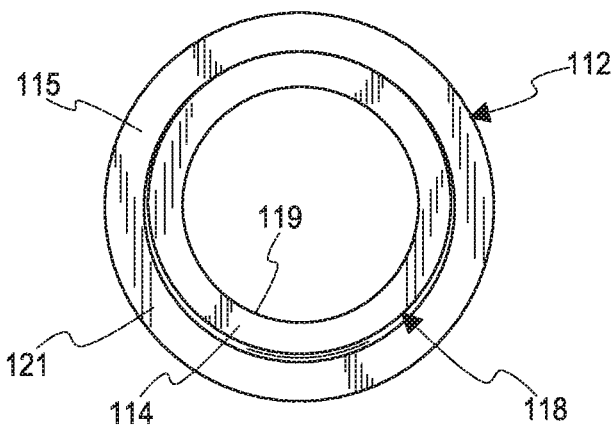
FIG. 1C is an elevated view of the proximal end of the drainage member.
Figure 1D:
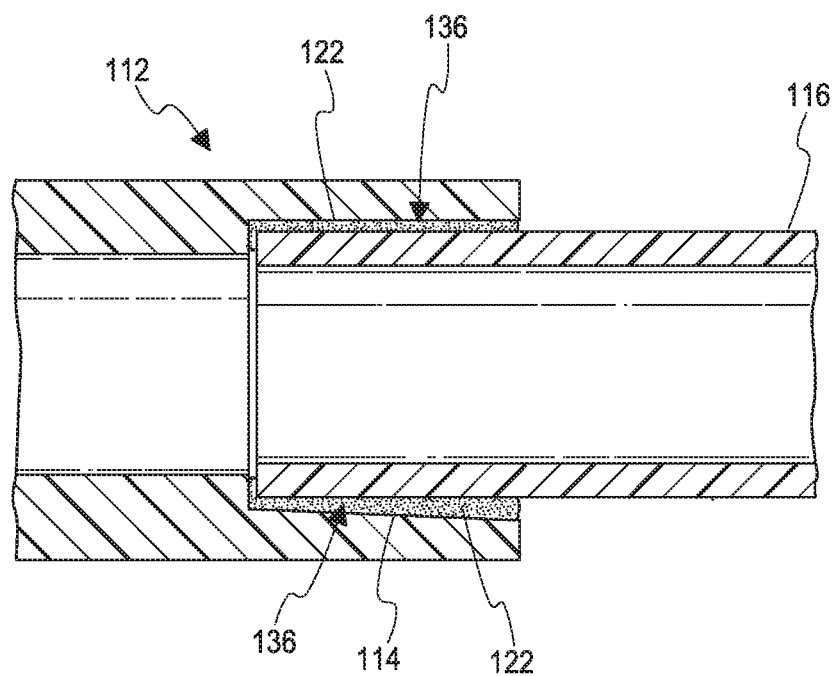
FIG. 1D is a cross-sectional view of the catheter tube attached to the catheter drainage member.

As shown in FIGS. 1B and 1C, a portion of the inner surface 114 is tapered (the tapered portion 118). The tapered portion 118 tapers outwardly from shoulder 119 to end wall 121. The tapered portion 118 of the inner surface 114 results in the inner surface 114 defining a non-symmetrical well 120 that has a wider side 118b and a narrower side 118a. The tapered portion 118 may be configured such that when the tube 116 is inserted angular momentum is applied to the adhesive 122 to distribute adhesive 122 about the well 120.

The tapered portion 118 controls the motion and flow of the adhesive 122 relative to the inner surface 114. Specifically, in the embodiment shown in FIG. 1, before the catheter tube 116 is inserted into the drainage member 112, adhesive 122 is placed on one side of the catheter tube 116, the adhesive side 116a. The adhesive side 116a is aligned with the wider side 118b of the tapered portion 118. The catheter tube 116 is then inserted into the drainage member 112. As the drainage member 112 and catheter tube 116 are coupled for attachment, the motion between the adhesive 122, the inner surface 114, and the tube 116 applies angular, axial, and radial momentum to the adhesive 122. The angular momentum distributes adhesive 122 about the well 120 and moves the adhesive 122 around the circumference or periphery of the tube 116, increasing the contact area between the adhesive 122 and the catheter tube 116, as well as increasing contact area between the adhesive 122 and the drainage member 112. Thus, the tapered portion 118, which defines the non-symmetrical well 120, facilitates increased adhesive coverage of the inner surface 114 with little or no rotation of the catheter tube 116 relative to the drainage member 112. The increased contact area caused by the tapered portion 118, leads to a stronger joint and a more efficient and effective manufacturing process.

FIG. 1 shows the drainage member 112 just prior to being assembled using a horizontal method. In the horizontal method the catheter tube 116 is placed horizontally relative to the drainage member 112 and adhesive 122 is applied directly onto the catheter tube 116. In the embodiment shown a small continuous amount of adhesive 122 is placed on the catheter tube 116. Alternatively, in other embodiments, a plurality of discontinuous dots of adhesive 122 may be placed on the catheter tube 116. The number of adhesive 122 dots may be any appropriate number. For example, two dots of adhesive may be placed on the catheter tube 116. The distance apart of the dots may be any appropriate distance. For example, when the tube 116 is cylindrical, the dots may be placed at 120 degrees from each other. In one embodiment, the dots may be placed at 2 and 10 o'clock wherein the reference point 12 o'clock is at the top of the tube. The tube 116 is attached to the drainage member by pushing the catheter tube 116 into the well 120 of the drainage member 112. The attachment also may occur by pushing the drainage member 112 into the catheter tube 116. When a UV cured adhesive 122 is used, after insertion of the tube and distribution of the adhesive, the joint may be formed by applying UV light 126 to cure the adhesive 122.

Figure 2A:
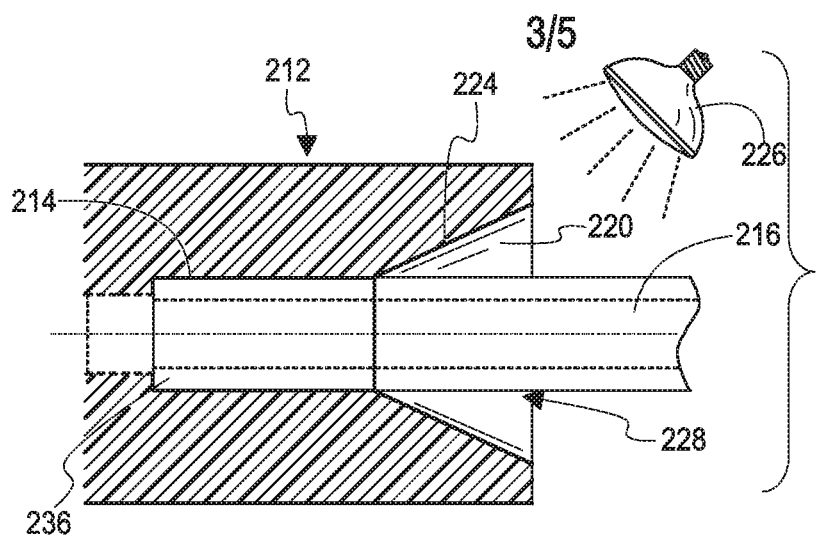
FIG. 2A is a cross-sectional view of an embodiment of a catheter drainage member having a well including a symmetrical conical cavity.

FIG. 2A shows an embodiment of the drainage member 212 where the drainage member 212 has a well 220 that includes a symmetrical conical cavity 224. The symmetrical conical cavity 224 facilitates adhesive 222 dispensing, while minimizing the amount of adhesive 222 used. Dispensing of adhesive 222 is controlled by positioning the adhesive dispensing needle in the well 220. The well 220 reduces and/or contains spillage and enables the adhesive 222 to flow into the adhesive gap 136 (or 236) where the adhesive is effective to bond the two components. Moreover, when a UV light 226 is present to cure the adhesive 222, the symmetrical conical cavity 224 may optimize UV light 226 penetration and curing speed. Curing speed is optimized due to the design of the symmetrical conical cavity 224. The symmetrical conical 224 cavity minimizes the volume of adhesive needed to affect a secure bond between the funnel 212 and the catheter tube 216. Smaller amounts of adhesive 222 require less UV energy to cure, so minimizing the amount of adhesive 222 can speed up the curing process, since less UV light energy is needed.

A gap 236 is defined in the space between the catheter tube 216 and the inner surface 214. The gap 236 is configured to receive adhesive 222 and allow bonding and an interference fit between the catheter tube 216 and the drainage member 212. The gap 236 is wider when the catheter tube 216 is smaller in size and narrower when the catheter tube 216 is larger in size.

Figure 2B:
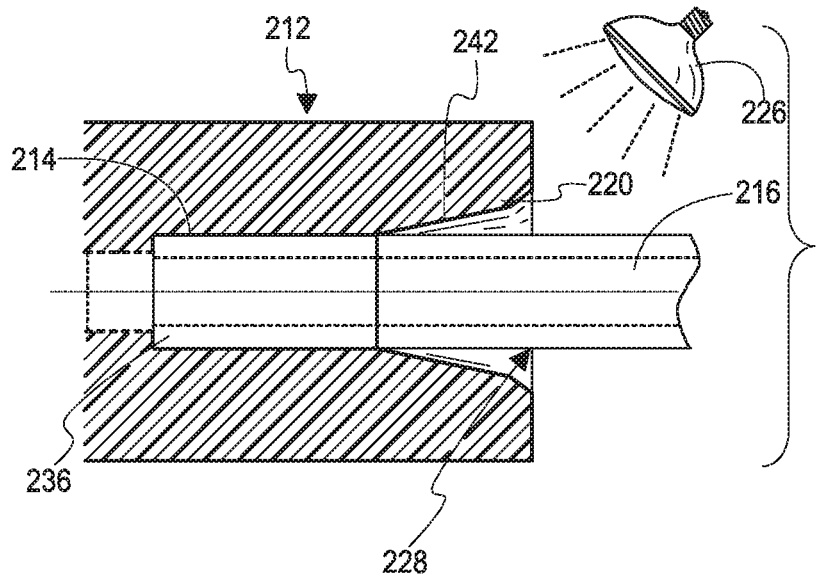
FIG. 2B is a cross-sectional view of an embodiment of a catheter drainage member having a well including a concave profile.

FIG. 2B shows an embodiment of the drainage member 212 where the drainage member 212 has a well 220 that includes a concave profile 242 and the inner surface 214 of the drainage member 212 has a convex profile. The concave profile 242 is configured to facilitate dispensing of the adhesive 222 and may minimize the amount of the adhesive 222 needed for attachment. Additionally, the concave profile 242 reduces the penetration length of UV light 226 beams, making it easier to cure the adhesive 222 at the joint 228. This embodiment also includes a gap 236, similar to that described above.

Figure 2C:
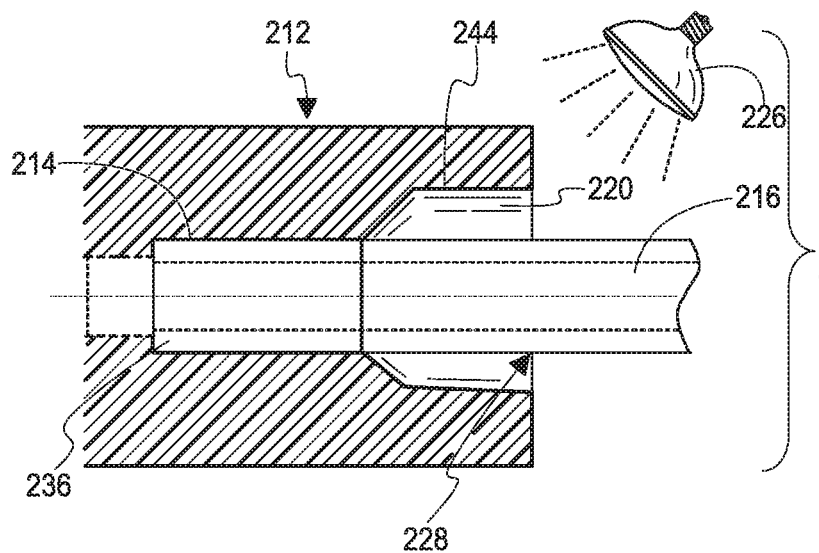
FIG. 2C is a cross-sectional view of an embodiment of a catheter drainage member having a well including a convex profile.

FIG. 2C shows an embodiment of the drainage member 212 where the drainage member 212 has a well 220 that includes a convex profile 244 and the inner surface 214 of the drainage member 212 has a concave profile. The convex profile 244 is configured to facilitate dispensing of the adhesive 222 and may be used in those embodiments wherein additional adhesive 222 is desired.

Figure 3:
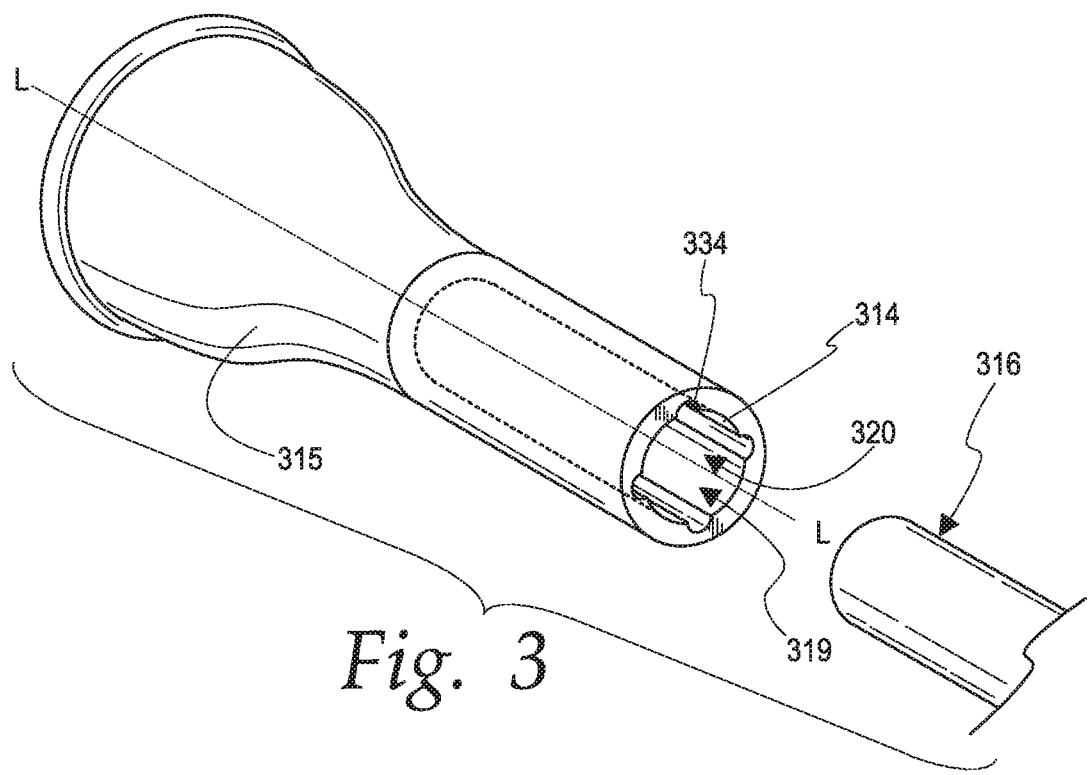
FIG. 3 is a perspective view of an embodiment of a catheter drainage member having axial channels.

FIG. 3 shows an embodiment of the drainage member 312 where the drainage member 312 includes a body 315 having a longitudinal axis L. The inner surface 314 includes at least one channel 334 extending in the direction of the longitudinal axis L. The at least one channel 334 is in communication with the well 320. Additionally, the at least one channel 334 may include a plurality of channels 334.

In the embodiment shown in FIG. 3, the drainage member 312 has four channels 334. Though this embodiment has four channels 334, other embodiments may have more than four channels 334 or less than four channels. The number of channels 334 may be selected according to the desired use. In FIG. 3 the channels 334 are axial channels that are aligned with the long axis L. At least one channel 334 extends from a proximal opening 319 in the drainage member 312. The channels 334 are configured to communicate with the well 320 and may be configured to communicate between the well 320 and the gap between the inner surface 314 of the drainage member 312 and the catheter tube 316, when the catheter tube 316 is located within the well 320. Furthermore, the channels 334 may communicate with each other. For example, the inner surface 314 of the drainage member 312 may include additional channels (not shown) that extend about the circumference of the inner surface 314 and connect the channels 334.

The channels 334 increase the volume of the well 320 by creating a pathway for a greater amount of adhesive 322 to fit between the catheter tube 316 and the drainage member 312. The increased amount of space created by the channels 334 allows a larger quantity of adhesive 322 to be moved into the gap between the inner surface 314 and the catheter tube 316 and to fill the surface area between the catheter tube 316 and the inner surface 314 of the drainage member 312. The greater amount of adhesive 322 in the gap may assist in creating a stronger bond between the catheter tube 316 and the drainage member 312. Thus, the channels 334 improve the distribution of adhesive 322 in the gap.

Any suitable method may be used to create the channels 334. One method may include using a profiled core pin to create the channels 334 in the long axis L of the drainage member 312. The channels 334 may be created as the drainage member 312 is being molded.

Figure 4A:
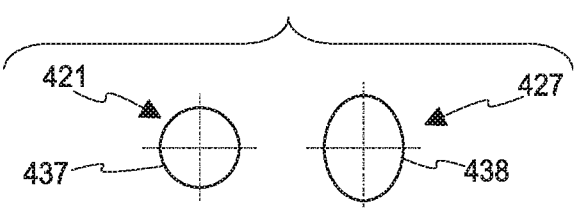
FIG. 4A is a cross-sectional view of an embodiment of a catheter drainage member, showing a profile change from a circular configuration to an oblong configuration.
Figure 4B:
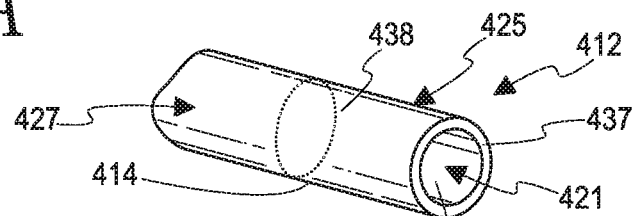
FIG. 4B is an enlarged perspective view of the drainage member of FIG. 4A, showing the drainage member without an inserted catheter tube.
Figure 4C:
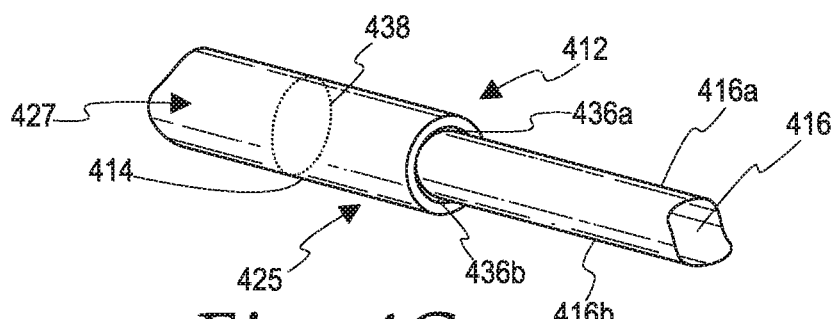
FIG. 4C is an enlarged perspective view of the drainage member of FIG. 4B, showing the drainage member with the catheter tube inserted.

FIGS. 4A-4C show an embodiment of the drainage member 412 where the well 420 defines an opening 421 and the inner surface 414 defines a profile 425. The profile 425 changes from a circular configuration 437 at the well opening 421 to an oblong configuration 438 at a section 427 distal from the opening 421. Thus, the profile 425 of the inner surface 414 is configured to change from the circular configuration 437 at the well opening 421 (without an inserted catheter tube 416) to the oblong configuration 438 when a catheter tube 416 is inserted into the drainage member 412. Thus, the drainage member 412 has different cross-sectional profiles at the well 420 and the distal section 427.

An enlarged view of the difference in profile shapes is shown in FIG. 4A. The shape of the well opening 421 with the circular configuration 437 is visible, and the shape of the distal section 427 with the oblong configuration 438 is visible.

FIG. 4B shows the drainage member 412 without the catheter tube 416 inserted. The circular profile 437 of the well 420 is visible, and the change to an oblong profile 438 at the distal section 427 is visible.

FIG. 4C illustrates the well 420 with the catheter tube 416 inserted. As shown in FIG. 4C, the catheter tube 416 and/or the well 420 may change shape as the catheter tube 416 passes through the oblong profile 438 of the distal section 427. The catheter tube 416 is compressed by the distal section 427. The compression causes the catheter tube 416 to make contact with the sides of the drainage member 412. The compressed catheter tube 416 also creates two spaces at the top and bottom of the well 420 (the glue gaps 436): a top gap 436a and a bottom gap 436b. Adhesive 422 may be placed on one or both sides of the catheter tube 416—the catheter tube top 416a and the catheter tube bottom 416b. A strong interference fit may be formed between the drainage member 412 and the catheter tube 416. The oblong profile 438 creates a mechanical bond between the sides of the compressed drainage member 412 which directly contact the catheter tube 416, while the gaps 436a, 436b create increased space for containing adhesive 422 to bond the top 416a and/or bottom 416b of the catheter tube 416 to the drainage member 412. Additionally, in one embodiment the oblong profile 438 may cause two gaps, such that one of the gaps (436a, 436b) is larger than the other. For example, in one embodiment the top gap 436a may be larger than the bottom gap 436b so that the top gap 436a has more space for receiving adhesive 422 than the bottom gap 436b. The uneven gap sizes create two different sized sites for dispensing adhesive 422. The different sized sites lend versatility to the drainage member 412.

Figure 5A:
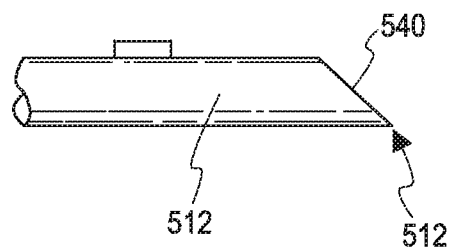
FIG. 5A shows a side view of an embodiment of a catheter drainage member having a sloped diagonal end profile.
Figure 5B:
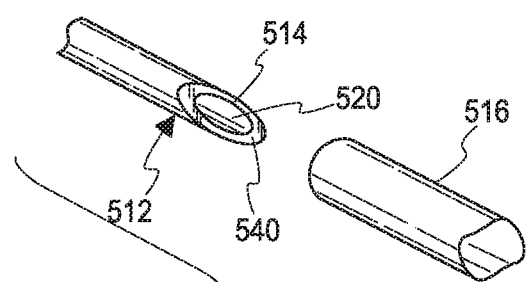
FIG. 5B shows a perspective view of the drainage member of FIG. 5A.

FIGS. 5A and 5B show an embodiment of the drainage member 512, where the drainage member 512 includes a proximal end portion 540 that has a sloped diagonal profile which defines a well 520 having a sloped diagonal end profile. FIG. 5A shows a side view of the drainage member 512 and FIG. 5B shows a perspective view of the drainage member 512. The sloped diagonal end 540 increases the volume of a standard circular shaped well by increasing the length of one side of the well 520. The diagonal end 540 deepens one side of the well 520 and creates a bigger space so that the well 520 is able to receive an increased amount of adhesive 522. The diagonal end 540 may be used with the horizontal dispensing method and in situations where a larger catheter tube 516 is attached to the drainage member 512.

Figure 6A:
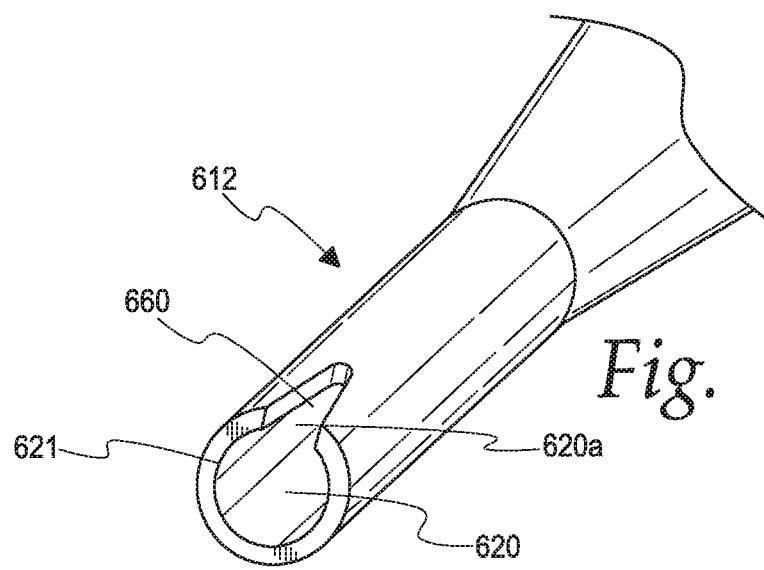
FIG. 6A is a perspective view of an embodiment of a catheter drainage member with a slot.
Figure 6B:
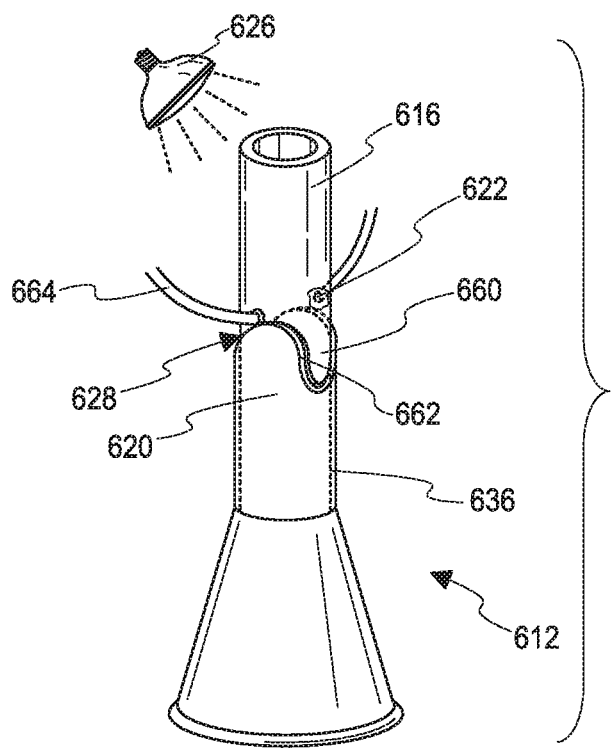
FIG. 6B is a cross-sectional side view of an embodiment of a catheter drainage member showing glue placed on peaks between slots.

FIG. 6A shows an embodiment of the drainage member 612 wherein the proximal end 621 of the drainage member 612 includes at least one slot 660. The slot 660 may be configured to extend from the proximal end 621 of the drainage member 612 toward the distal end. Using a slot 660 increases portions of the well 620 without having to increase the entire portion of the drainage member 612 defining the well 620. That is, the slot 660 provides the benefits of a larger well 620 with use of less material. Also, the increased portions of the well 620 provide an increase in volume of the well 620, which in turn allows for the well 620 to receive an increased amount of adhesive 622. The slot 660 may be utilized with the horizontal dispensing method wherein the axis of the catheter tube 616 and the axis of the drainage member 612 are horizontal to the ground when being assembled and the adhesive 622 is dispensed onto the tube 616 and in line with the slot 660. As shown in FIG. 6B, the drainage member 612 may also be used with a vertical method of adhesive 622 dispensing. In the vertical method, the catheter tube 616 is inserted into the well 620 of the drainage member 612, followed by dispensing the adhesive 622 into the well 620. FIG. 6B shows the adhesive 622 being dispensed by two glue dispensers 664 on at least one peak 662 between the slot 660. After the adhesive 622 is dispensed, the adhesive 622 moves around the catheter tube 616 and then may move along the gap 636. The flow of adhesive 622 is driven primarily by gravity, excess surface free energy of the adhesive 622, and injection pressure of the adhesive 622. Adhesives 622, with appropriate surface viscosity and surface tension may be selected. Once the adhesive 622 is dispensed, a UV light 626 may be used to cure the adhesive 622.

The drainage member (112, 212, 312, 412, 512, 612) embodiments described above may be at least partially made of a rigid polymeric material. For example, at least a surface of the drainage member may be molded or extruded from plasticized polyvinyl chloride (PVC), polyethylene, polypropylene, or other suitable, biocompatible polymeric materials.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter drainage member configured to be attached to a catheter tube, the drainage member comprising:
    a body having an inner surface and a longitudinal axis extending between a proximal end of the body and a distal end of the body;
    a non-symmetrical well defined by the inner surface of the body, the body having an end wall with a proximal opening configured to receive the catheter tube and an adhesive into the non-symmetrical well, the inner surface of the body having a tapered portion extending outwardly from a shoulder at a distal end of the non-symmetrical well to the end wall at a proximal end of the non-symmetrical well, and the non-symmetrical well having a cross-section that is non-symmetrical in a plane that is perpendicular to the longitudinal axis of the body and parallel to the end wall of the body, the cross-section having a narrower side and a wider side; and
    wherein the well is configured to selectively distribute the adhesive between the inner surface and the tube.

2. The drainage member of claim 1, wherein the drainage member is configured to have an annular gap between the inner surface and the catheter tube.

3. The drainage member of claim 1, wherein the well is configured to evenly distribute the adhesive.

4. The drainage member of claim 1, wherein the tapered portion is configured such that when the tube is inserted angular momentum is applied to the adhesive to distribute adhesive about the well.

5. A urinary catheter, comprising:
    a catheter tube; and
    a drainage member attached to a distal end of the catheter tube, the drainage member comprising:
        a body having an inner surface and a longitudinal axis extending between a proximal end of the body and a distal end of the body;
        a non-symmetrical well defined by the inner surface of the body, the body having an end wall with a proximal opening configured to receive the catheter tube and an adhesive into the non-symmetrical well, the inner surface of the body having a tapered portion extending outwardly from a shoulder at a distal end of the non-symmetrical well to an end wall at a proximal end of the non-symmetrical well, and the non-symmetrical well having a cross-section that is non-symmetrical in a plane that is perpendicular to the longitudinal axis of the body and parallel to the end wall of the body, the cross-section having a narrower side and a wider side; and
    wherein the well is configured to selectively distribute the adhesive between the inner surface and the tube.

6. The urinary catheter of claim 5, wherein the drainage member includes an annular gap between the inner surface and the catheter tube.

7. The urinary catheter of claim 6, wherein the annular gap has a non-uniform width at the proximal end of the drainage member.

8. The urinary catheter of claim 5, wherein the well is configured to evenly distribute the adhesive.

* * * * *